United States Patent [19]
Vasta

[11] Patent Number: 5,277,874
[45] Date of Patent: Jan. 11, 1994

[54] MOLD APPARATUS FOR THERMALLY PROCESSING A RIMMED, SEALED, FOOD-FILLED, PLASTIC CONTAINER

[76] Inventor: Gloria J. Vasta, 5207 Saum St., Fairborn, Ohio 45324

[21] Appl. No.: 478,699

[22] Filed: Feb. 12, 1990

[51] Int. Cl.⁵ .......................... B01L 9/00; A61L 2/04; A23L 3/10
[52] U.S. Cl. .......................... 422/104; 422/1; 422/25; 422/26; 422/102; 422/297; 422/300; 99/426; 99/483; 249/89; 249/121; 426/407; 426/412
[58] Field of Search .............. 422/1, 25-26; 422/102, 104, 297, 300; 249/82, 121; 99/356, 426, 439, 483; 426/407, 412, 401, 325, 232

[56] References Cited
U.S. PATENT DOCUMENTS

| | | | |
|---|---|---|---|
| 2,629,148 | 2/1953 | Kollsman | 422/297 |
| 2,932,386 | 4/1960 | Ushkow | 249/121 |
| 2,959,488 | 11/1960 | Van de Kerke | 422/1 |
| 2,964,889 | 12/1960 | Oelze et al. | 426/407 |
| 2,980,248 | 4/1961 | Embring | 249/121 |
| 3,215,538 | 11/1965 | Sada | 422/25 |
| 3,339,878 | 9/1967 | Lind | 249/121 |
| 3,379,120 | 4/1968 | Fogle | 99/439 |
| 3,414,229 | 12/1968 | Norberg | 242/121 |
| 3,481,688 | 12/1969 | Craig et al. | 422/25 |
| 3,606,995 | 9/1971 | Van den Hemel | 422/25 |
| 4,216,241 | 8/1980 | Thompson | 249/121 |
| 4,450,122 | 5/1984 | Gallina | 249/121 |
| 4,739,699 | 4/1988 | Nelson | 99/483 |

Primary Examiner—James C. Housel
Assistant Examiner—Jan M. Ludlow
Attorney, Agent, or Firm—John F. A. Earley; John F. A. Earley, III

[57] ABSTRACT

A process and apparatus for the commercial sterilization of thin-walled, high-profile plastic containers, which are hermetically sealed with an easy-peel aluminum foil/plastic-coated lid stock material. The apparatus is a rack of molds, each mold having a recessed groove to support the lip of the plastic container and a mold lid having a rigid portion covering the lid and a resilient portion inside the rigid portion to permit the lid of the plastic container to expand in a controlled manner during sterilization. The rigid portion of the mold lid can be angled to fit the contour of the expanded container lid.

10 Claims, 7 Drawing Sheets

MOLD APPARATUS FOR THERMALLY PROCESSING A RIMMED, SEALED, FOOD-FILLED, PLASTIC CONTAINER

BACKGROUND OF THE INVENTION

1. Field of the Invention

This invention relates to equipment and processes for thermally processing food products, and more particularly concerns apparatuses and processes for thermally processing food products hermetically sealed in plastic containers, especially thin-walled, high-profile plastic containers.

2. Description of the Prior Art

The thermal processing of sealed, food-filled, thin-walled, high-profile plastic containers presents some unique problems not previously encountered with rigid metal containers. Since most plastic materials currently approved for contact with food tend to lose their structural definition (shape) as temperatures increase above 170 degrees Fahrenheit, maintaining a balance between the internal pressure inside the plastic container and the external pressure on the plastic container inside the sterilizer during the sterilization process is very critical for maintaining the shape of the container and for insuring that the seal remains intact. If pressure imbalance between the internal pressure inside the plastic container and the external pressure on the outside of the plastic container become too great during thermal processing, the container bulges and/or panels. This is a major problem in the industry, since a bulged or panelled container is not sold, but rather is rejected by the food packer and thrown away.

One method of producing acceptable food-filled plastic containers with good seals is to constantly monitor for pressure differences between the pressure inside the plastic container and the pressure outside the plastic container in the processing vessel which occur during thermal processing, and then to correspondingly adjust the processing controls to balance these pressures.

Such a method of balancing the pressures inside and outside the plastic container require: (a) different pressure profiles for different food materials, since different foods usually have different thermal expansion properties; and (b) longer ramping pressure profiles during the heating cycle and the cooling cycle of the sterilization process, which significantly reduces the production capacity (throughput) of the processing unit during production.

This method of thermally processing foods packed and sealed in plastic containers by balancing pressures inside and outside the sealed, food-filled plastic container is currently used with varying degrees of success by food processors, and the best results using this method are achieved with low-profile plastic trays and thick-walled plastic cups which, for the most part, are still being closed with a metal lid using the conventional double-seam seal.

Under the known technology, cup-like plastic containers that are closed either by conduction or induction sealing using a thin foil lidding material require over-pressure during the sterilization process not only to preserve the container shape but to prevent the lid from bursting at the seal track. Since the foil lid does not use a double-seam seal, it is very susceptible to rupturing if the internal pressure inside the container is not compensated for during thermal processing.

Since the amount of air in the sealed, food-filled plastic container has an effect on the internal pressure inside the plastic container, a foil or plastic lid material which, is either preformed or shaped during the closing step, is used to eliminate any headspace between the product and the lid. Forming the lid in this manner creates a condition in the package known as a "hydropack" which allows the internal pressure to be accurately calculated during the sterilization cycle. The drawback with this method is that it requires the use of expensive lidding material and slower sealing speeds.

Further, since fill weights tend to vary to some degree during the filling of food products into the plastic containers, the amount of headspace in the container and, correspondingly, the amount of internal pressure created in the container during thermal processing varies from container to container. Thus, the pressure profile used for a particular thermal processing cycle does not compensate for all the variations in fill weights and headspace of each container being processed, and therefore a certain percentage of the containers are distorted (e.g., bulged or panelled walls or ruptured seals) during the thermal processing.

Material redistribution and shrinkage may also occur during thermal processing at elevated temperatures, particularly plastic containers having a plurality of layers in its walls. Further, if not controlled, rippling of the walls of the plastic container may occur during thermal processing at elevated temperatures, which also causes package distortion.

Moreover, the known technology for thermally processing sealed, food-filled plastic containers is very complex, relying on sophisticated process controls and equipment for balancing pressure inside the plastic container with the pressure on the plastic container outside the plastic container to preserve the seal and to limit distortion of the plastic container. Further, the known technology does not effectively thermally process sealed, food-filled, thin-walled, high-profile plastic containers, since thermal processing of such containers using the known technology usually results in some distortion of the containers.

In summary, there are a multitude of problems that are associated with the thermal processing of sealed, food-filled plastic containers at elevated temperatures, and these problems include:
flexibility of plastic at elevated temperatures;
elaborate and long processing cycles;
expensive lidding material;
slow sealing operations with preformed lids;
distorted containers due to pressure imbalances;
material redistribution and shrinkage;
material cost for plastic;
limited selection of thermal processing equipment.

SUMMARY OF THE INVENTION

It is an object of the invention to provide apparatuses for thermally processing food products hermetically sealed in plastic containers that prevent panelling and bulging of the container walls and rupturing of the container seal.

Another object of the invention is to provide a simplified, cost-effective method for thermally processing food products hermetically sealed in plastic containers, especially thin-walled, high-profile plastic containers, without the problems of bulging and panelling of the container walls and rupturing of the container seal.

These and other objects are accomplished by providing a rack for holding a plurality of rimmed, plastic containers during a sterilization process, said containers containing food and being sealed with a peelable lid, that comprises a first plate member, a plurality of molds formed in the first plate member for holding the plastic containers, a lip formed in the upper end portion of each mold defining an opening in the mold through which the plastic container is placed into and removed from the mold, a recessed groove formed in each lip for receiving the rim of the plastic container, each mold being shaped such that the mold is in contact with substantially all of the outer surface of the plastic container, and mold lid means for securing the plastic containers in the molds during the sterilization process and for permitting the lid of the plastic container to expand outwardly during a sterilization process and to contract to substantially its original shape after completion of the sterilization process.

The rack contains a plurality of mold apparatus for holding a rimmed, sealed, food-filled plastic container, and each mold apparatus comprises a mold for holding the plastic container, a lip formed in the upper end portion of the mold defining an opening in the mold through which the plastic container is placed into and removed from the mold, a recessed groove formed in the lip for receiving the rim of the plastic container, the mold being shaped such that the mold is in contact with substantially all of the outer surface of the plastic container, and mold lid means for securing the plastic container in the mold during the sterilization process and for permitting the lid of the plastic container to expand outwardly during the sterilization process and to contract to substantially its original shape after completion of the sterilization process.

The method of sterilizing food contained in a plastic rimmed container and sealed in the plastic rimmed container with a peelable lid includes the steps of placing the sealed plastic container containing the food in a mold that is shaped such that the mold is in contact with substantially all the outer surfaces of the plastic container. After securing the edge portion of the lid of the plastic container against the rim of the plastic container, which sits in a recessed groove in the lip of the mold, by appropriate mold lid means, the sealed plastic containers are subjected to sterilization processing. During the sterilization processing, the lid of the plastic container is permitted to expand outwardly while outward expansion of the plastic container is blocked.

The present invention reduces significantly the complexity of the total system needed to carry out the sterilization process by providing rigid external support to the plastic container which allows the container to behave like a rigid metal package during the sterilization process. The shape of the rigid mold apparatus corresponds substantially to the shape of the plastic container, and allows for the controlled expansion of the plastic container, if needed or desired, into the shape of the mold during sterilization. The invention also provides a mechanical means for reinforcing the seal track of the container by sandwiching the container seal between a recessed lip ledge of the mold and the non-flexible, non-resilient portion of the mold lid means to prevent the rupturing of the seal caused by excess pressure during the sterilization process. Since the rigid mold apparatus prohibits and/or limits the thermal expansion of the plastic container, the need for sophisticated pressure controls and for the balancing of pressures during the heating and cooling cycles of the sterilization process is eliminated.

The invention reduces the sterilization cycle time by as much as fifty percent which translates into faster production speeds and reduced manufacturing costs. The invention significantly reduces the wall thickness of the plastic container needed to maintain the shape of the container. Further, since wall thickness of the container may be reduced, less plastic is needed to manufacture each container, which represents a savings in cost of materials.

Moreover, thin-walled, high-profile plastic containers may be thermally processed at elevated temperatures (220° F.-260° F.) without risk of distortion or ruptured seals.

DETAILED DESCRIPTION

Figure 1:
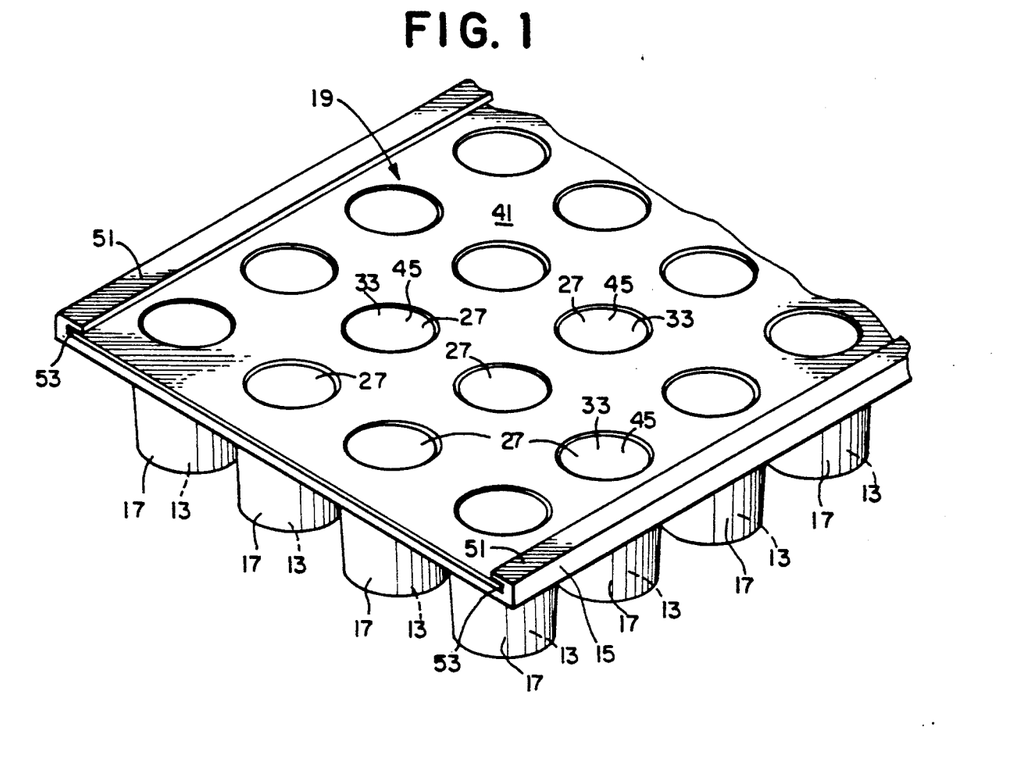
FIG. 1 is a view in perspective of a rack constructed in accordance with this invention.
Figure 3:
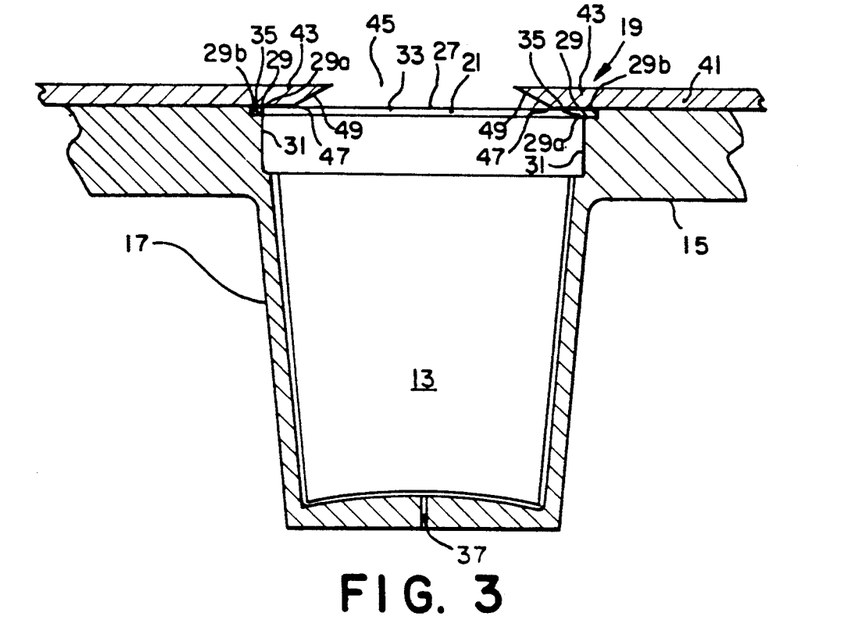
FIG. 3 is an enlarged cross-sectional view taken along the lines and arrows 3—3 of FIG. 1 and illustrates a mold apparatus containing a rimmed plastic container prior to sterilization processing.
Figure 4:
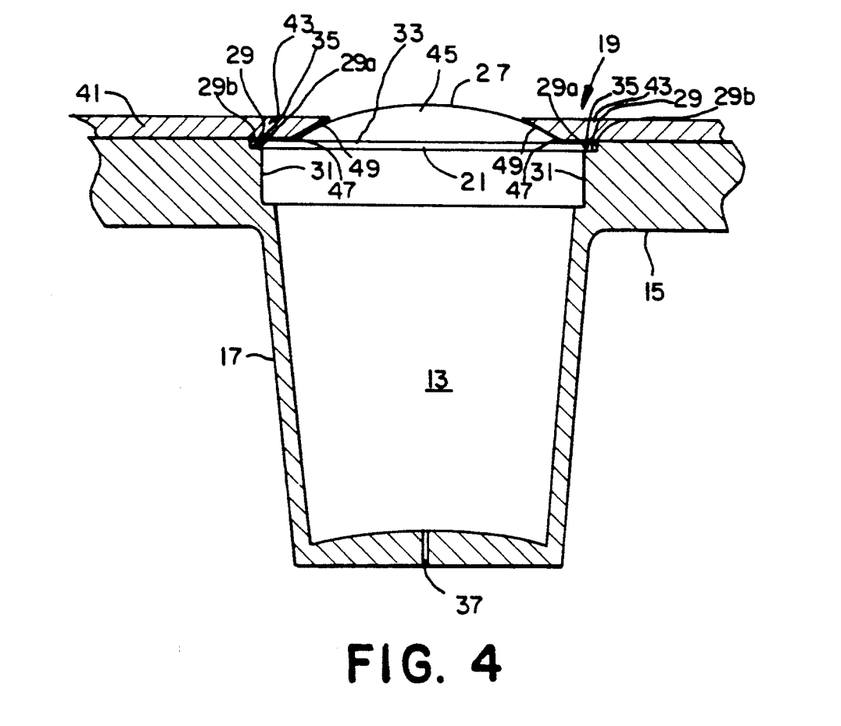
FIG. 4 is an enlarged cross-sectional view and shows the mold apparatus of FIG. 3 during sterilization processing.

Turning now to the drawings, there is shown in FIGS. 1, 3 and 4 a rack 11 for holding a plurality of rimmed plastic containers 13 during a sterilization process that comprises a first plate member 15, a plurality of molds 17 formed in the first plate member 15 for holding the plastic containers 13, and mold lid means 19 for securing the plastic container 13 in the mold 17 during the sterilization process.

Figure 2:
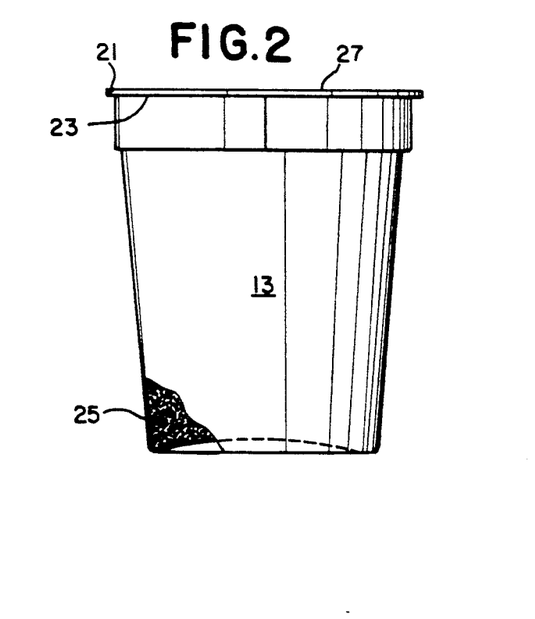
FIG. 2 is a view in front elevation of a rimmed plastic container having a peelable lid.

Plastic containers 13 (FIG. 2) are cup-like in shape and have an outwardly extending rim 21 at its upper end portion 23. Food 25 is sealed inside the plastic container 13 by a peelable lid 27. Preferably, the seal extends along the entire surface of the rim 21, but a narrower seal may be used if desired.

Each mold 17 is provided with a lip 29 (FIGS. 3 and 4) that is formed in the upper end portion 31 of each mold 17 which defines an opening 33 in the mold 17 through which the plastic container 13 is placed into and removed from the mold 17.

A recessed groove 35 is formed in each lip 29 for receiving the rim 21 of the plastic container 13, and groove 35 is defined by horizontal lip ledge 29a and vertical lip wall 29b that extends upwardly from the outer portion of the lid ledge 29a.

A vent 37 is provided in the bottom wall 39 of each mold 17 for relieving trapped air when plastic container 13 is placed in the mold 17. Vent 37 also facilitates removal of plastic container 13 from mold 17 after completion of the sterilization process by preventing vacuum from forming in mold 17 as plastic container 13 is removed from the mold 17 after thermal processing.

Each mold 17 is shaped such that it is in contact with substantially all the outer surface of the plastic container 13 when the plastic container 13 is inserted into the mold 17.

Mold lid means 19 is provided for securing the plastic containers 13 in the molds 17 during the sterilization process and for permitting the peelable lid 27 of the plastic container 13 to expand outwardly during the sterilization process and to contract to substantially its original shape after completion of the sterilization process.

Mold lid means 19 includes a second plate member 41 that has a non-flexible, non-resilient portion 43 for covering the lip 29 of each mold 17. A plurality of openings 45 are provided in second plate member 41, and openings 45 are aligned with a corresponding opening 33 in each mold 17 when second plate member 41 is secured to first plate member 15.

Second plate member 41 has a beveled edge 47 at the lower periphery of each opening 45 so that upon expansion of container lid 27 during thermal processing, container lid 27 is not cut by being in contact with a sharp edge at opening 45.

Second plate member 41 also has a slanted peripheral portion 49 at the periphery of each opening 45 which matches the contour of the bulge of the container lid 27 during thermal processing.

Referring to FIG. 1, clamping members 51 are provided at the left and right edges of first plate member 15 for securing the second plate member 41 to the first plate member 15. To secure the plate members 15 and 41 together, second plate member 41 is slid over first plate member 15 with the left and right edges of second plate 41 sliding into a channel 53 formed by each clamping member 51 until plate members 15 and 41 are properly aligned with one another, that is, until the openings 45 in second plate member 41 are properly aligned over openings 33 in mold 17 of first plate member 15.

In operation, after a container 13 has been filled with food and has been sealed with peelable lid 27, it is placed in a mold 17. The air that is trapped inside the mold 17 as plastic container 13 is placed therein escapes through vent 37.

Second plate member 41 is then secured to first plate member 15 by sliding second plate member 41 over first plate member 15 such that the side edge portions of second plate member 41 are secured in the clamping members 51, thereby securing the first plate member 15 onto the second member plate 41.

The rack 11 is then placed in a sterilizer and subjected to the sterilization process.

As the pressure inside each container 13 builds during the sterilization process, outward expansion of each plastic container 13 is blocked by the mold 17 that the container 13 sits in.

Since the sealed portion of peelable lid 27, together with rim 21, sits in recessed groove 35 and is mechanically secured in place by, but not overly compressed by, non-flexible, non-resilient portion 43 of second plate member 41, it is protected from being compressed too severely (e.g., by second plate member 43) during thermal processing. Non-flexible, non-resistent portion 43 of second plate member 41 merely reinforces the seal between peelable lid 27 and rim 21. Further, by placing the seal in the groove 35, the seal area is not subjected to the extreme pressure inside the container 13 during thermal processing. The depth of groove 35, that is, the height of lip wall 29b, is such that rim 21 and the lid seal are secured in place, but not crushed, between lip ledge 29a and second plate member portion 43.

As container 13 is being processed in the sterilizer, as is shown in FIG. 4, the peelable lid 27 expands or bulges outwardly through opening 45 in second plate 41 due to the internal pressure building up inside container 13. In effect, the peelable lid 27 acts as a diaphragm by expanding outwardly as the pressure builds up inside container 13 during the sterilization process and by contracting inwardly as the pressure inside container 13 is reduced after the sterilization process.

The resulting product is a sealed plastic container 13. Its walls have not bulged or paneled and its seal has not ruptured.

Figure 5:
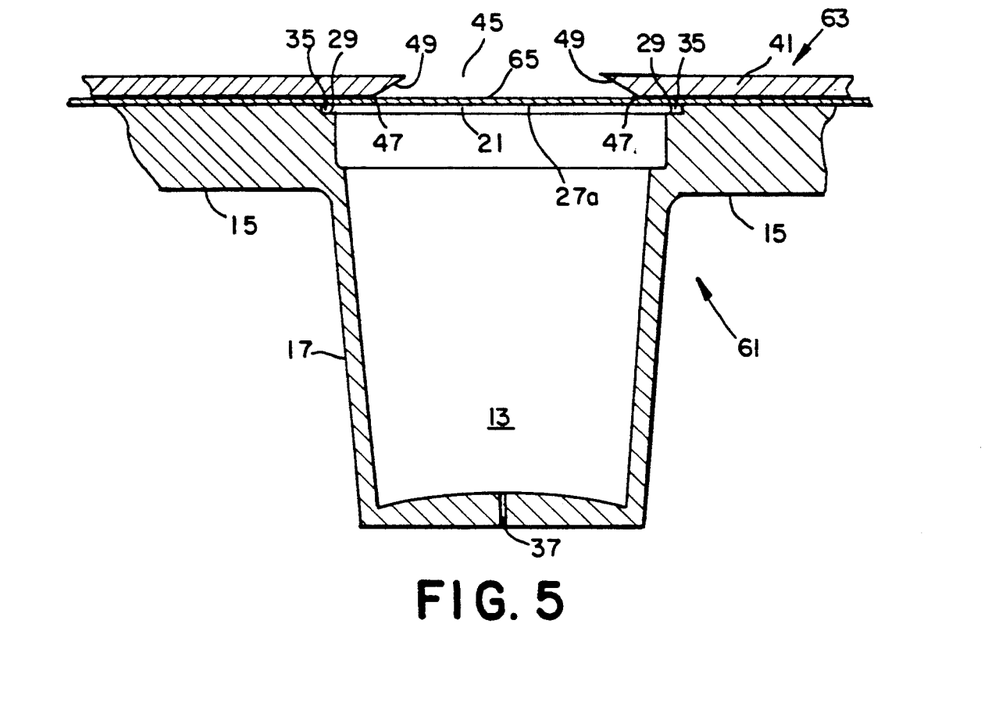
FIG. 5 is an enlarged cross-sectional view of an alternative embodiment of the invention and illustrates a mold apparatus containing a rimmed plastic container prior to sterilization processing.
Figure 6:
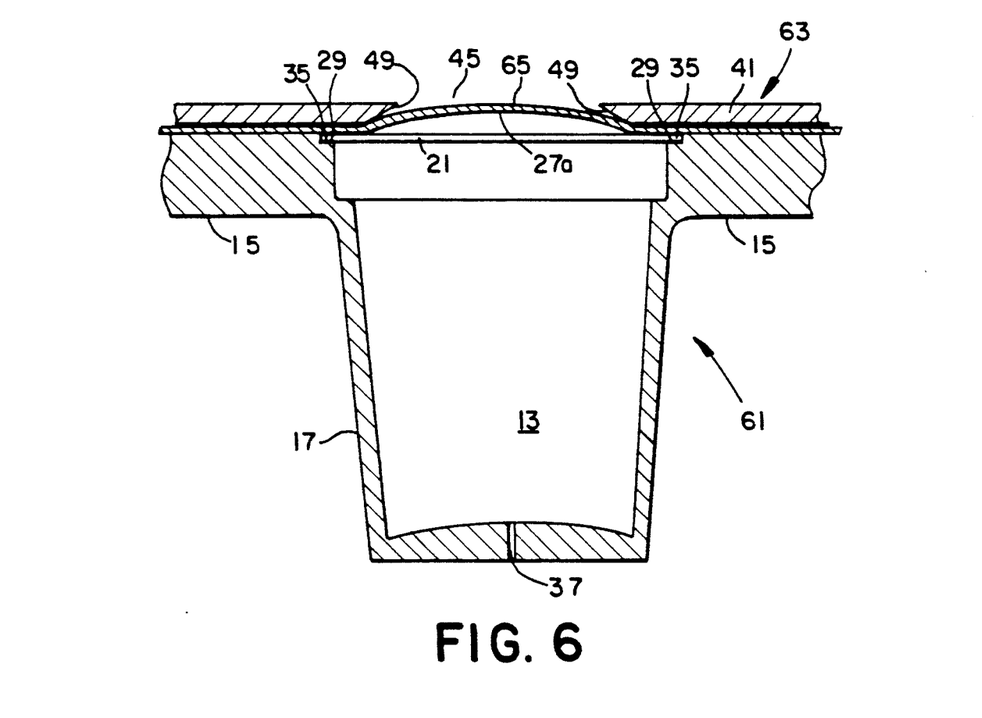
FIG. 6 is an enlarged cross-sectional view and shows the mold apparatus of FIG. 5 during sterilization processing.

FIGS. 5 and 6 illustrate an alternative embodiment of the invention, rack 61, which preferably is used when thermal processing plastic containers sealed with a thin lid material. In this embodiment, a different mold lid means 63 is used for securing the plastic containers 13 in molds 17 during the sterilization process and for permitting the peelable lid 27a of plastic container 13 to expand outwardly during the sterilization process and to contract to substantially its original shape after completion of the sterilization process.

Mold lid means 63 includes the second plate member 41 described in the first embodiment of the invention, together with a light, resilient metallic plate 65 that is affixed to the underside of second plate member 41 and that extends over openings 45 in second plate member 41.

During thermal processing (FIG. 6), the container lid 27a bulges or expands outwardly into contact with metallic plate 65 and then pushes metallic plate 65 outwardly with it. Here, the metallic plate 65 acts as a supporting wall for the bulging container lid 27a preventing it from expanding too much and rupturing.

Because metallic plate 65 is resilient, it, in conjunction with container lid 27a, acts as a diaphragm by expanding outwardly as the pressure builds up inside container 13 during the sterilization process and by contracting inwardly as the pressure inside container 13 is reduced after the sterilization process.

The resulting product is a sealed plastic container that contains food. Its walls have not bulged or panelled and its seal has not ruptured.

Figure 7:
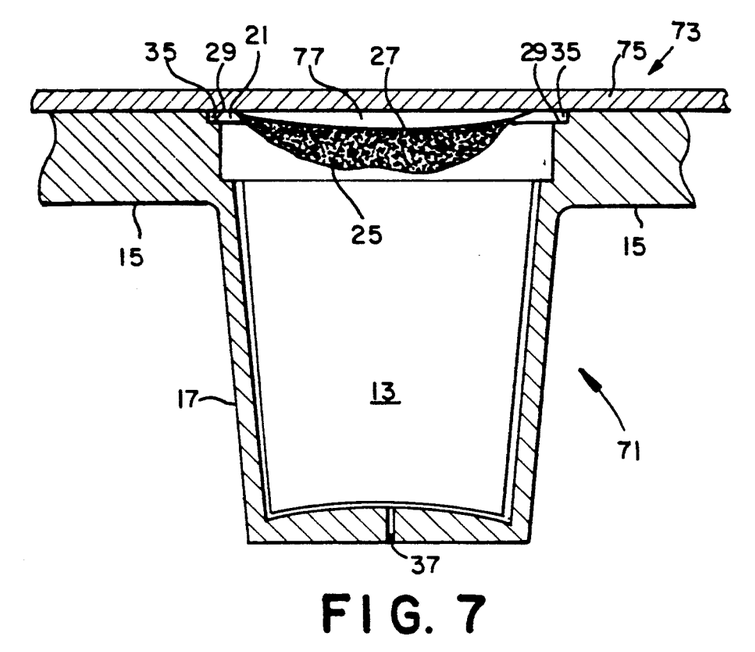
FIG. 7 illustrates another embodiment of the invention and is an enlarged cross-sectional view of a mold apparatus having a sealed container resting therein.
Figure 8:
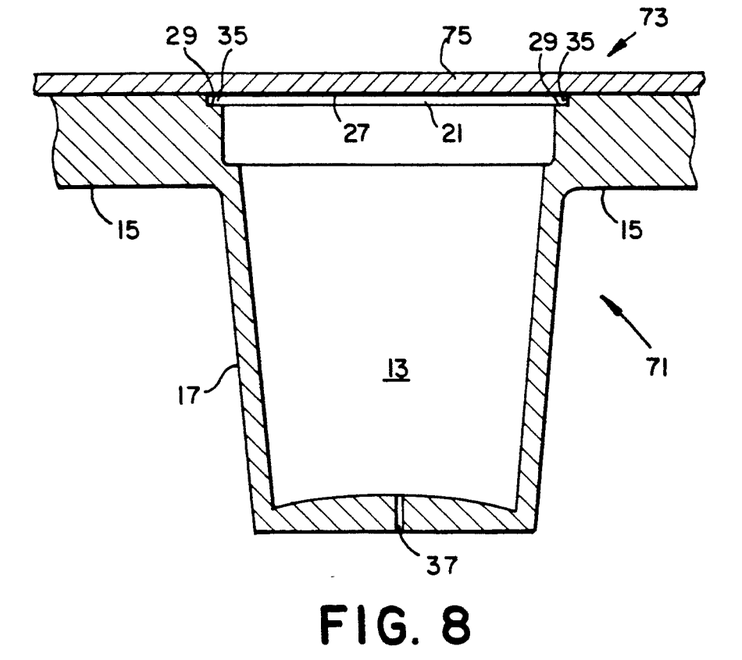
FIG. 8 is an enlarged cross-sectional view and shows the mold apparatus of FIG. 7 during sterilization processing.

FIGS. 7 and 8 illustrate another alternative embodiment of the invention, rack 71, which preferably is used when thermal processing plastic containers 13 that contain low-acid food products with particulates. In this embodiment, a different mold lid means 73 is used for securing the plastic container 13 in molds 17 during the sterilization process and for permitting the peelable lid 27 of plastic container 13 to expand outwardly during the sterilization process and to contract to substantially its original shape after completion of the sterilization process.

Mold lid means 73 includes a cover plate member 75 that is non-flexible and non-resilient, and that is secured to first plate member 15 as described in the first embodiment of the invention.

In this embodiment, the food 25 is vacuum-packed into container 13, thereby resulting in a container lid 27 that is concave in shape. Because the container lid 27 is concave, there is sufficient space 77 between container lid 27 and cover plate member 75 to permit sufficient expansion of container lid 27 during thermal processing.

Figure 9:
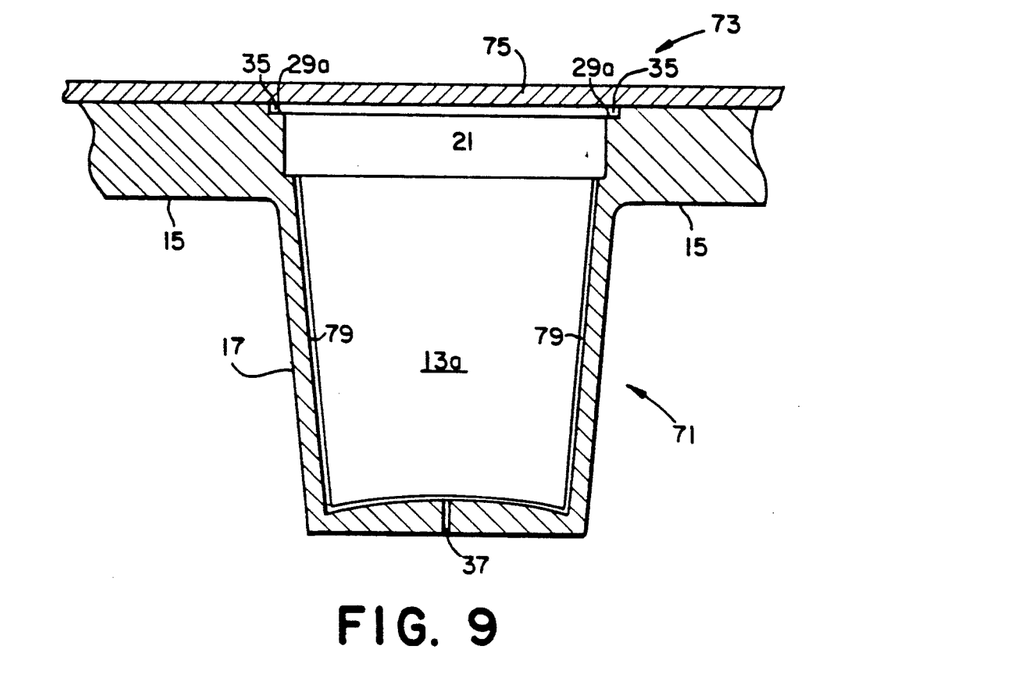
FIG. 9 is another enlarged cross-sectional view of the mold apparatus shown in FIGS. 7 and 8 having a different sealed plastic container resting therein.
Figure 10:
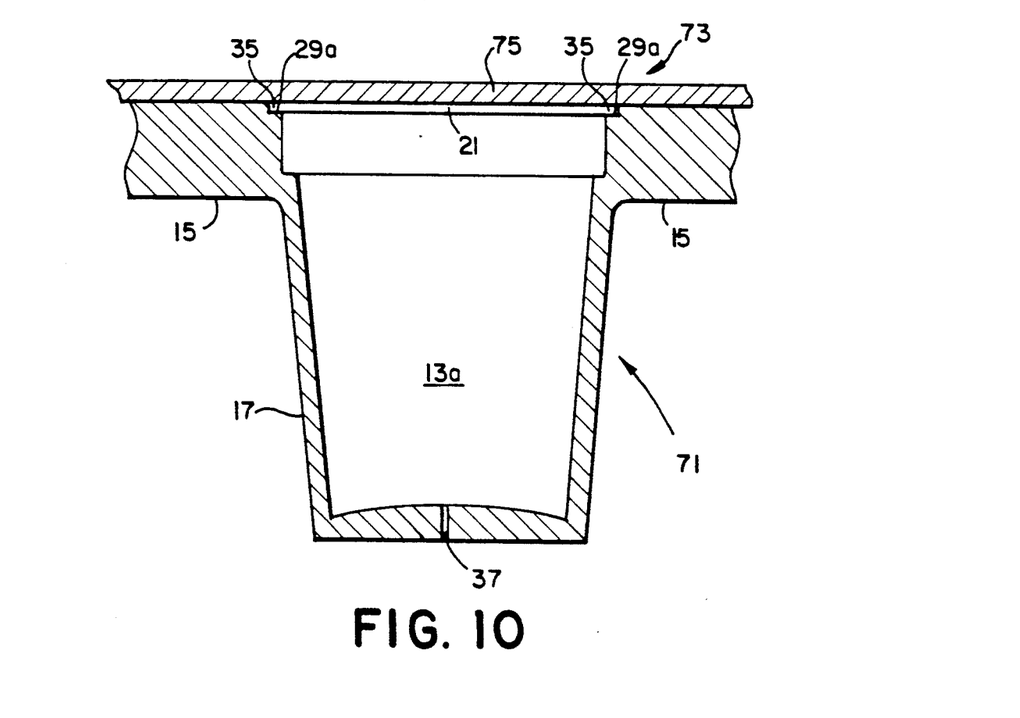
FIG. 10 is an enlarged cross-sectional view and shows the mold apparatus of FIG. 9 during sterilization processing.

Alternatively, as illustrated in FIGS. 9 and 10, a plastic container 13a is thermally processed in rack 71. Plastic container 13a has a shape that substantially corresponds to the shape of mold 17, but is sized such that there is a small space 79 between the outer surface of container 13a and the walls of the mold 17 when container 13a sits inside mold 17.

During thermal processing, as shown in FIG. 10, the walls of the container 13a expand outwardly due to the internal pressure built up inside the container 13a. Throughout thermal processing, the seal area of container 13a is mechanically reinforced by being secured in groove 35 between lip ledge 29a and cover plate member 75. However, the seal area is not crushed.

When container 13a is subsequently cooled, it maintains its expanded shape; that is, the shape of the mold 17.

Figure 11:
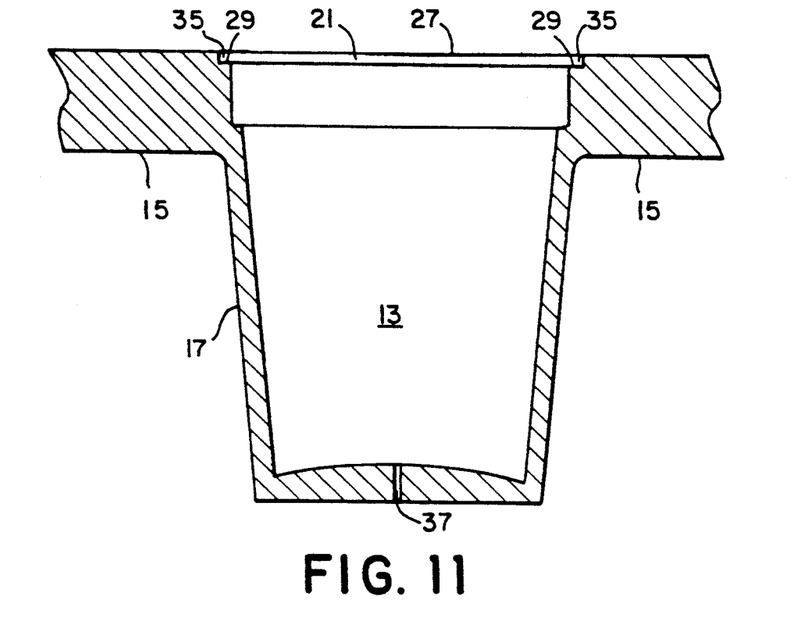
FIG. 11 illustrates another alternative embodiment of the invention and shows an enlarged cross-sectional view of a mold apparatus having a sealed container resting therein.
Figure 12:
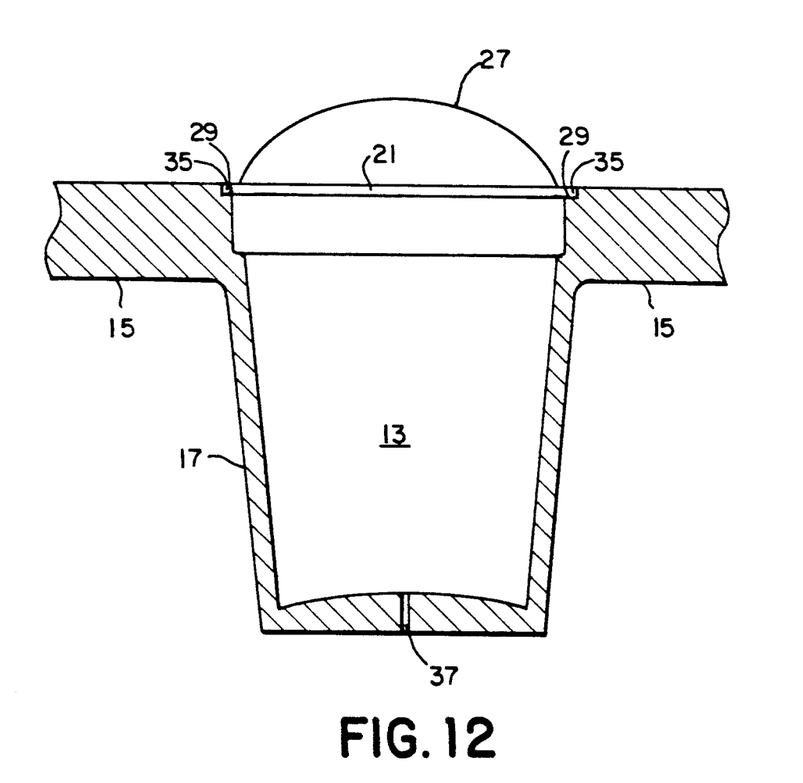
FIG. 12 is an enlarged cross-sectional view and shows the mold apparatus of FIG. 11 during thermal processing.

FIGS. 11 and 12 illustrate another embodiment of the invention. In this embodiment, no mold lid means is used to secure the plastic container 13 in the mold 17. Rather, standard overpressure (e.g., 40 pounds per square inch gauge) from the sterilization unit is used in place of a mold lid means, with the overpressure reinforcing the seal area of container 13 but permitting the container lid 27 to expand or bulge outwardly during thermal processing (FIG. 12). Expansion of the walls of container 13 is blocked by mold 17, preventing bulging of the container walls.

Figure 13:
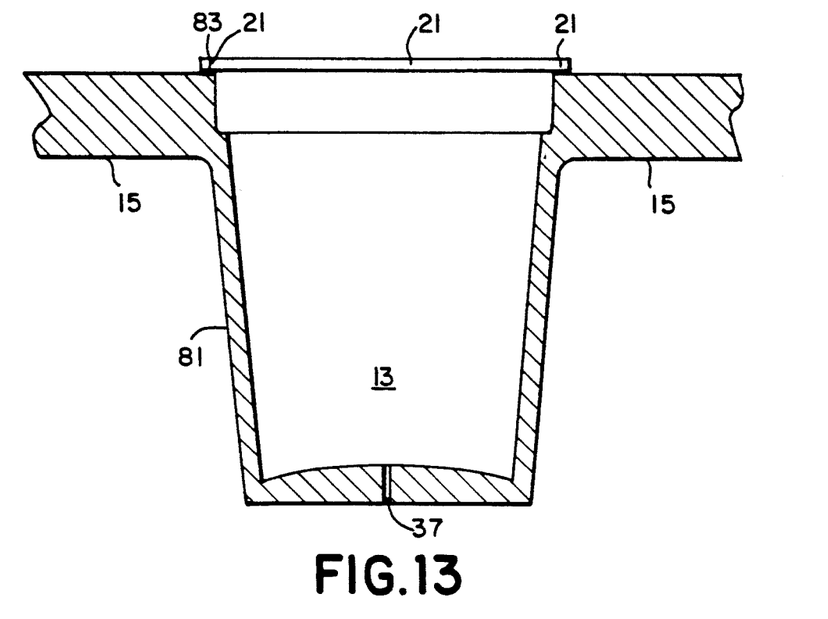
FIG. 13 illustrates another embodiment of the invention and shows an enlarged cross-sectional view of a mold apparatus having a sealed container resting therein.
Figure 14:
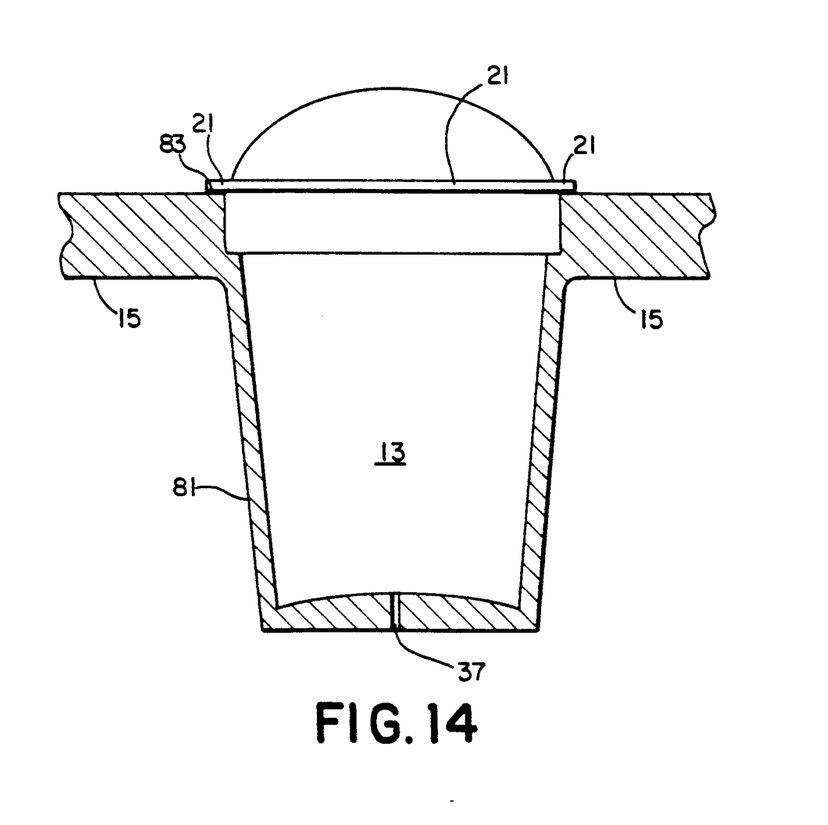
FIG. 14 is an enlarged cross-sectional view of the mold apparatus of FIG. 13.

FIGS. 13 and 14 show another embodiment of the invention. In this embodiment, a container 13 is placed in a mold 81. Unlike mold 17, mold 81 does not have a recessed groove in its lip 83, and no mold lid means is used to secure the plastic container 13 in the mold 81. In operation, rim 21 of plastic container 13 rests on lip 83 of mold 81, and standard overpressure from the sterilization unit is used in place of a mold lid means. Use of standard overpressure reinforces the seal area of container 13 without crushing the seal area.

Regarding thermal processing of plastic containers, as illustrated in FIGS. 11, 12, 13 and 14, if steam or air and steam are used as the heating medium in the sterilization unit, only overpressure is needed to secure the container 13 in place in the rack. However, if water is used as the heating medium in the sterilization unit, additional securing means, such as pins over the rim of the plastic containers 13, may be necessary to prevent container 13 from floating out of the mold 17.

The method of sterilizing food 25 contained in a plastic rimmed container 13, 13a and sealed in the plastic rimmed container 13, 13a with a peelable lid 27, 27a, comprises the steps of placing the sealed plastic container 13, 13a containing the food 25 in a mold 17, 81 that is shaped such that the mold 17, 81 is in contact with substantially all the outer surfaces of the plastic container 13, 13a, holding the edge portion of the lid 27, 27a of the plastic container 13, 13a securely against the rim 21 of the plastic container 13, 13a, sterilizing the sealed plastic container 13, 13a and the food 25 contained therein, permitting the lid 27, 27a of the plastic container 13, 13a and/or the side walls of the plastic container 13, 13a to expand outwardly during sterilization, and blocking outward expansion of the plastic container 13, 13a beyond a set point during sterilization. Further, the process may include the steps of limiting the outward expansion of the lid 27, 27a of the plastic container 13, 13a during sterilization to prevent rupturing of the lid 27, 27a.

For example, low acid food products with particulates are either filled hot or cold into the plastic cups depending on the type of blending operation. The filled cups are then sealed with a peelable foil lid material 27 with or without any additional vacuum being added before the sealing step is completed. The filled and sealed cups are placed in the appropriate metal mold apparatus, are covered with the mold lid means 19, 63, 73 (or held in place with overpressure) such that the seal area is reinforced but not crushed during thermal processing, and are thermally processed in either a batch or continuous sterilizer. The sterilizing medium can either be steam, steam/air, or water depending on the type of sterilizer.

During the sterilization cycle the food product begins to heat and internal cup pressure begins to rise as a result. As the temperature and pressure increase, the cup expands to the exact dimensions of the mold apparatus and the flexible lid bulges upwardly to a predetermined extent to relieve the excess pressure inside the plastic container. The amount of upward movement of the flexible lid is restricted by the top plate of the mold apparatus, or overpressure, in order to protect the seal track and preserve seal integrity.

Once the heating step of the sterilization cycle is completed, the product enters the cooling step. During the cooling step, the mold apparatus and the plastic cup begin to cool. As this happens the plastic material regains its rigidity at a faster rate than the product cools and before the internal pressure inside the plastic container is reduced. The resulting effect is a perfectly shaped container with a good seal.

It should be understood that the shape of the mold may vary from the cup-like shape illustrated in this application, and that other shapes of the mold, so long as the containers being placed therein correspond to the shape of the mold, are in the scope of this invention. For example, a container having a box shape may be used so long as the shape of the mold has a box shape that corresponds to the box shape of the plastic container.

ADVANTAGES

Bonding to the lidding material to the plastic cup must be strong enough to withstand the rigors of processing and still provide ease of peel to allow the container to be easily opened. By having the seal mechanically held in place, but not crushed between two plates, a good seal is maintained that withstands the rigors of processing and still provides ease of peel to allow the container to be easily opened.

I claim:

1. A rack for holding a plurality of rimmed plastic containers during a sterilization process, said containers containing food and being sealed with a peelable lid, comprising
   a first plate member,
   a plurality of molds formed in the first plate member constructed and arranged so as to hold plastic containers which contain food and are sealed with a peelable lid,
   a lip formed in an upper end portion of each mold defining an opening in the mold through which the plastic container is placed into and removed from the mold,
   a recessed groove formed in each lip for receiving the rim of the plastic container,
   each mold being shaped such that the mold is in contact with substantially all of the outer surface of the plastic container when the plastic container is placed in the mold, and
   mold lid means for securing the plastic containers in the molds during the sterilization process and for permitting the lid of the plastic container to expand outwardly during the sterilization process and to contract to substantially its original shape after completion of the sterilization process,
   the mold lid means including a second plate member,
   said second plate member having a non-flexible, non-resilient portion constructed and arranged so as to cover the lip of each mold, and
   said second plate member having flexible, resilient portions constructed and arranged so as to cover the opening in each mold defined by the lip formed in the upper end portion of each mold.

2. The rack of claim 1,
   said second plate member having a plurality of openings that are aligned with the opening in each mold defined by the lip formed in the upper end portion of each mold,
   said plurality of openings of said second plate member each being defined by a slanted peripheral surface disposed at the periphery of each opening, said surface matching a contour of the expanded lid of the plastic container during the sterilization process.

3. The rack of claim 1, further including
   means for locking the mold lid means to the molds of the rack.

4. A mold apparatus for holding a rimmed plastic container during a sterilization process, said container containing food and being sealed with a peelable lid, comprising
   a mold constructed and arranged so as to hold a plastic container which contains food and is sealed with a peelable lid,
   a lip formed in the upper end portion of the mold defining an opening in the mold through which the plastic container is placed into and removed from the mold,
   a recessed groove formed in the lip constructed and arranged so as to receive the rim of the plastic container,
   the mold being shaped such that the mold is in contact with substantially all of the outer surface of the plastic container, and
   mold lid means for securing the plastic container in the mold during the sterilization process and for permitting the lid of the plastic container to expand outwardly during the sterilization process and to contract to substantially its original shape after completion of the sterilization process,
   said mold lid means including a mold lid having a non-flexible, non-resilient portion constructed and arranged so as to cover the lip of the mold and a flexible, resilient portion constructed and arranged so as to cover the opening in the upper end portion of the mold.

5. The mold apparatus of claim 4, said non-flexible, non-resilient portion having a slanted peripheral surface disposed at the periphery of said opening, said surface matching a contour of the expanded lid of the plastic container during the sterilization process.

6. The mold apparatus of claim 4, further including
   means for locking the mold lid means to the lip of the mold.

7. A rack for holding a plurality of rimmed plastic containers during a sterilization process, said containers containing food and being sealed with a peelable lid, comprising
   a first plate member,
   a plurality of molds formed in the first plate member constructed and arranged so as to hold plastic containers which contain food and are sealed with a peelable lid,
   a lip formed in an upper end portion of each mold defining an opening in the mold through which the plastic container is placed into and removed from the mold,
   a recessed groove formed in each lip for receiving the rim of the plastic container,
   each mold being shaped such that the mold is in contact with substantially all of the outer surface of the plastic container when the plastic container is placed in the mold, and
   mold lid means for securing the plastic containers in the molds during the sterilization process and for permitting the lid of the plastic container to expand outwardly during the sterilization process and to contract to substantially its original shape after completion of the sterilization process,
   said mold lid means including a second plate member having a first portion constructed and arranged so as to cover the lip of each mold and the opening in the upper end portion of each mold above the lip,
   said first portion of said second plate member being non-flexible and non-resilient,
   said second plate member further including a flexible, resilient second portion constructed and arranged so as to cover the opening in the upper end portion of each mold.

8. A mold apparatus for holding a rimmed plastic container during a sterilization process, said container containing food and being sealed with a peelable lid, comprising
   a mold constructed and arranged so as to hold a plastic container which contains food and is sealed with a peelable lid,
   a lip formed in the upper end portion of the mold defining an opening in the mold through which the plastic container is placed into and removed from the mold, a recessed groove formed in the lip constructed and arranged so as to receive the rim of the plastic container, the mold being shaped such that the mold is in contact with substantially all of the outer surface of the plastic container, and mold lid means for securing the plastic container in the mold during the sterilization process and for permitting the lid of the plastic container to expand outwardly during the sterilization process and to contract to substantially its original shape after completion of the sterilization process, said mold lid means including a mold lid having a first portion constructed and arranged so as to cover the lip of the mold and the opening in the upper end portion of the mold above the lip, said first portion of said mold lid being non-flexible and non-resilient, said mold lid further including a flexible, resilient second portion constructed and arranged so as to cover the opening in the upper end portion of the mold.

9. A rack for holding a plurality of rimmed plastic containers during a sterilization process, said containers containing food and being sealed with a peelable lid, comprising a first plate member, a plurality of molds formed in the first plate member constructed and arranged so as to hold plastic containers which contain food and are sealed with a peelable lid, a lip formed in an upper end portion of each mold defining an opening in the mold through which the plastic container is placed into and removed from the mold, a recessed groove formed in each lip for receiving the rim of the plastic container, each mold being shaped such that the mold is in contact with substantially all of the outer surface of the plastic container when the plastic container is placed in the mold, and mold lid means for securing the plastic containers in the molds during the sterilization process and for permitting the lid of the plastic container to expand outwardly during the sterilization process and to contract to substantially its original shape after completion of the sterilization process, said mold lid means including a second plate member, said second plate member having a non-flexible, non-resilient portion constructed and arranged so as to cover the lip of each mold, and said second plate member having a plurality of openings that are aligned with the opening in each mold defined by the lip formed in the upper end portion of each mold, said plurality of openings of said second plate member each being defined by a slanted peripheral surface disposed at the periphery of each opening, said surface matching a contour of the expanded lid of the plastic container during the sterilization process.

10. A mold apparatus for holding a rimmed plastic container during a sterilization process, said container containing food and being sealed with a peelable lid, comprising a mold constructed and arranged so as to hold a plastic container which contains food and is sealed with a peelable lid, a lip formed in the upper end portion of the mold defining an opening in the mold through which the plastic container is placed into and removed from the mold, a recessed groove formed in the lip constructed and arranged so as to receive the rim of the plastic container, the mold being shaped such that the mold is in contact with substantially all of the outer surface of the plastic container, and mold lid means for securing the plastic container in the mold during the sterilization process and for permitting the lid of the plastic container to expand outwardly during the sterilization process and to contract to substantially its original shape after completion of the sterilization process, the mold lid means including a mold lid having an opening therein such that the mold lid covers substantially only the lip of the mold, said opening in the mold lid being defined by a slanted peripheral surface disposed at the periphery of the opening, said surface matching a contour of the expanded lid of the plastic container during the sterilization process.

* * * * *